United States Patent [19]

Innis et al.

[11] Patent Number: 5,075,216
[45] Date of Patent: Dec. 24, 1991

[54] METHODS FOR DNA SEQUENCING WITH THERMUS AQUATICUS DNA POLYMERASE

[75] Inventors: Michael A. Innis, Moraga; Kenneth B. Myambo, Pittsburg; David H. Gelfand; Mary Ann D. Brow, both of Oakland, all of Calif.

[73] Assignee: Cetus Corporation, Emeryville, Calif.

[21] Appl. No.: 249,367

[22] Filed: Sep. 23, 1988

[51] Int. Cl.⁵ .............................................. C12P 19/34
[52] U.S. Cl. ........................................ 435/6; 435/91; 435/810; 436/501; 436/808; 536/27; 935/16; 935/17; 935/18; 935/78; 935/88
[58] Field of Search .............................. 435/6, 91, 810; 436/501, 808; 536/27; 935/16, 17, 18, 78, 88

[56] References Cited

U.S. PATENT DOCUMENTS

| | | | |
|---|---|---|---|
| 4,683,202 | 7/1987 | Mullis | 435/91 |
| 4,795,699 | 1/1989 | Tabor et al. | 435/5 |
| 4,921,794 | 5/1990 | Tabor et al. | 435/91 |
| 5,001,050 | 3/1991 | Blanco et al. | 435/5 |

FOREIGN PATENT DOCUMENTS

| | | |
|---|---|---|
| 0258017 | 3/1988 | European Pat. Off. . |
| 351138 | 1/1990 | European Pat. Off. . |
| 9008839 | 8/1990 | PCT Int'l Appl. . |

OTHER PUBLICATIONS

Chait et al. (1988) Nature, vol. 333, pp. 477–478.
Simpson et al. (Feb., 1988) Biochem. and Biophys. Res. Comm., vol. 151, No. 1, pp. 487–492.
Miyusawa et al. (1986) Nuc. Acids Res., vol. 14, No. 3, pp. 1319–1324.
Sanger et al., Dec. 1977, *Proc. Natl. Acad. Sci. U.S.A.* 74:5463–5467.
Mills et al., May 1979, *Proc. Natl. Acad. Sci. U.S.A.* 76(5):2232–2235.
Yanisch-Perron et al., 1985, *Gene* 33:103–119.
Barr et al., 1986, *BioTechniques* 4(5):428–432.
Smith et al., Jun. 12, 1986, *Nature* 321:674–679.
Wrischnik et al., 1987, *Nuc. Acids Res.* 15(2):529–542.
Prober et al., Oct. 16, 1987, *Science* 238:336–341.
Ansorge et al., 1987, *Nuc. Acids Res.* 15(11):4593–4602.
Tabor et al., Jul. 1987, *Proc. Natl. Acad. Sci. U.S.A.* 84:4767–4771.
Wong et al., Nov. 26, 1987, *Nature* 330:384–386.
Toneguzzo et al., 1988, *BioTechniques* 6(5):460–469.
Tindall et al., 1988, *Biochem.* 27:6008–6013.
Engelke et al., Jan. 1988, *Proc. Natl. Acad. Sci. U.S.A.* 85:544–548.
Saiki et al., Jan. 29, 1988, *Science* 239:487–491.
Stoflet et al., Jan. 29, 1988, *Science* 239:491–494.
New England BioLab's Catalog Update, Oct. 1987.
Promega advertisement, product update bulletin and Taq DNA polymerase certificate of analysis.
Stratagene advertisement.
Gyllensten et al., Oct. 1988, *Proc. Natl. Acad. Sci. U.S.A.* 85:7652–7656.
Innis et al., Dec. 1988, *Proc. Natl. Acad. Sci. U.S.A.* 85:9436–9440.
Nakamaye et al., preprint.
Hunkapiller, Jun. 2, 1988, *Nature* 333:477–478.
Shengyu et al., May 1987, *Scientia Sinica* XXX(5):503–506.
Heiner et al., May 27, 1988, Preliminary Draft.
McConlogue et al., Oct. 25, 1988, *Nuc. Acids Res.* 16(20):9869.

Primary Examiner—Robert A. Wax
Assistant Examiner—Ardin H. Marschel
Attorney, Agent, or Firm—Stacey R. Sias; Kevin R. Kaster

[57] ABSTRACT

Dideoxynucleotide DNA sequencing methods can be dramatically improved by utilizing the DNA polymerase from *Thermus aquaticus* to catalyze the primer extension reactions.

31 Claims, 3 Drawing Sheets

FIG. 3A
FIG. 3B
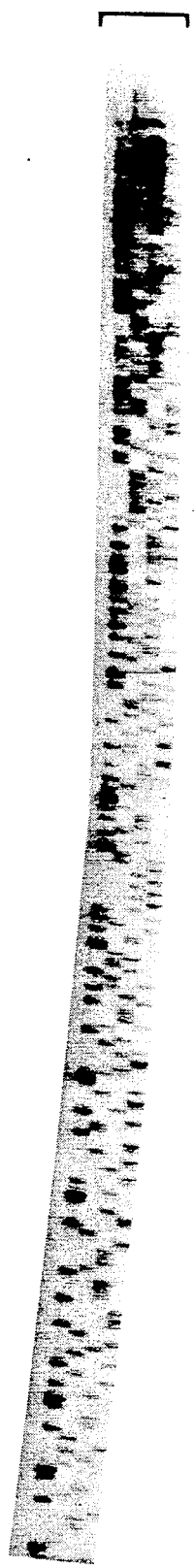
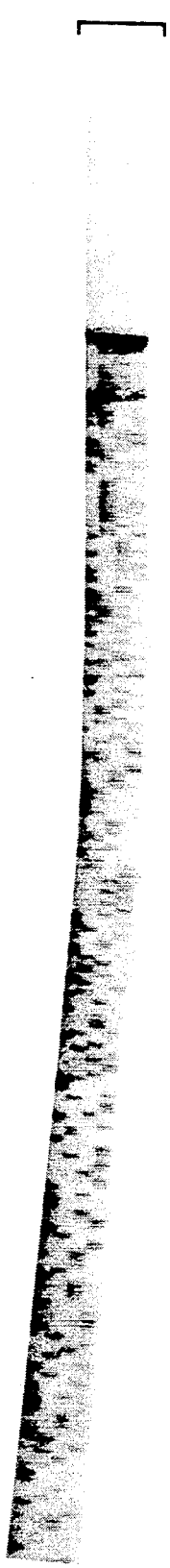

METHODS FOR DNA SEQUENCING WITH THERMUS AQUATICUS DNA POLYMERASE

BACKGROUND OF THE INVENTION

1. Field of the Invention

The present invention provides methods for DNA sequencing utilizing the thermostable DNA polymerase, Taq polymerase, of *Thermus aquaticus*. DNA sequencing methods are of great practical utility in the fields of molecular biology, genetics, medical diagnostic technology, and forensics. The importance of DNA sequencing is evidenced by the significant commercial activity centered about the production and marketing of reagents and automated instruments for sequencing nucleic acids.

2. Description of Related Disclosures

DNA sequencing by the Sanger dideoxynucleotide method (Sanger et al., 1977, *Proc. Natl. Acad. Sci. USA* 74:5463-5467) has undergone significant refinement in recent years, including the development of novel vectors (Yanisch-Perron et al., 1985, *Gene* 33:103-119), base analogs (Mills et al., 1979, *Proc. Natl. Acad. Sci. USA* 76:2232-2235, and Barr et al., 1986, *BioTechniques* 4:428-432), enzymes (Tabor et al., 1987, *Proc. Natl. Acad. Sci. USA* 84:4763-4771), and instruments for partial automation of DNA sequence analysis (Smith et al., 1986, *Nature* 321:674-679; Prober et al., 1987, *Science* 238:336-341; and Ansorge et al., 1987, *Nuc. Acids Res.* 15:4593-4602). The basic dideoxy sequencing procedure involves (i) annealing an oligonucleotide primer to a suitable single or denatured double stranded DNA template; (ii) extending the primer with DNA polymerase in four separate reactions, each containing one α-labeled dNTP or ddNTP (alternatively, a labeled primer can be used), a mixture of unlabeled dNTPs, and one chain-terminating dideoxynucleoside-5'-triphosphate (ddNTP); (iii) resolving the four sets of reaction products on a highresolution polyacrylamide-urea gel; and (iv) producing an autoradiographic image of the gel that can be examined to infer the DNA sequence. Alternatively, fluorescently labeled primers or nucleotides can be used to identify the reaction products. Known dideoxy sequencing methods utilize a DNA polymerase such as the Klenow fragment of *E. coli* DNA polymerase I, reverse transcriptase, or a modified T7 DNA polymerase. Protocols for sequencing with these enzymes, however, do not work with Taq polymerase.

Introduction of commercial kits has vastly simplified the art, making DNA sequencing a routine technique for any laboratory. However, there is still a need in the art for sequencing protocols that work well with nucleic acids that contain secondary structure such as palindromic hairpin loops and with G+C-rich DNA, which can form compressions in the DNA through Hoogsteen bond formation. Such DNA typically performs poorly in prior art sequencing protocols and can exhibit aberrant gel migration patterns that also interfere with sequence determination. In addition, there is a need for sequencing methods that can generate DNA sequence information over a long segment of DNA from one sequencing reaction. Currently, different sequencing methods must be used to generate both short and long sequence products. The present invention, as described more fully below, dramatically improves the art of DNA sequencing by, in one aspect, generating both short and long sequencing products in a single sequencing reaction.

The current commercial instruments address the "backend" of the sequencing process: non-isotopic detection and computerized data collection and analysis. Such developments have led many investigators to undertake large-scale sequencing projects, and to consider the sequencing of the entire human genome. The ultimate success of large-scale sequencing projects will depend upon further improvements in the speed and automation of the technology. These include developing alternative methods for handling the "front-end" of the process, i.e., automating the preparation of DNA templates and the performance of the sequencing reactions, and the present method provides a means for fully automating this frontend of the process.

One technique which appears to be ideally suited for automating DNA preparation is the selective amplification of DNA by the polymerase chain reaction (PCR), a method disclosed in U.S. Pat. No. 4,683,202. Methods for performing PCR are disclosed in pending Ser. No. 063,647, filed June 17, 1987, which is a continuation-in-part (CIP) of Ser. No. 899,513, filed Aug. 22, 1986, now abandoned, which is a CIP of Ser. No. 828,144, filed Feb. 7, 1986, which issued as U.S. Pat. No. 4,683,195, and which is a CIP of Ser. No. 791,308, filed Oct. 25, 1985, which issued as U.S. Pat. No. 4,683,202, and which is a CIP of abandoned Ser. No. 716,975, filed Mar. 28, 1985, all of which are incorporated herein by reference. PCR involves repeated cycles of (i) heat denaturation of the DNA, (ii) annealing of two oligonucleotide primers that flank the DNA segment to be amplified, and (iii) extension of the annealed primers with DNA polymerase. With this method, segments of single-copy genomic DNA can be amplified more than 10 million fold with very high specificity and fidelity. The PCR product can then either be subcloned into a vector suitable for sequence analysis or, alternatively, purified PCR products can be sequenced as disclosed by Engelke et al., 1988, *Proc. Natl. Acad. Sci. USA* 85:544-548; Wong et al., 1987, *Nature* 330:384-386; and Stoflet et al., 1988, *Science* 229:491-494.

Saiki et al., 1988, *Science* 239:487-494, demonstrate that Taq DNA polymerase greatly simplifies the PCR procedure. Because this polymerase has a broad temperature optimum centered around 75° C. and can survive repeated incubations at 95° C., fresh enzyme need not be added after each PCR cycle. Use of Taq DNA polymerase at high annealing and extension temperatures increases the specificity, yield, and length of products that can be amplified, and thus increases the sensitivity of PCR for detecting rare target sequences. Methods for isolating and producing recombinant Taq polymerase are disclosed in pending U.S. patent application Ser. No. 143,441, filed Jan. 12, 1988, which is a CIP of Ser. No. 063,509, filed June 17, 1987, which issued as U.S. Pat. No. 4,889,818, which is a CIP Ser. No. 899,241, now abandoned, filed Aug. 22, 1986, each of which is incorporated herein by reference.

Inverse PCR is a variation of PCR in which the plasmid containing the target template is digested with a restriction endonuclease and recircularized to access flanking sequences for amplification and is fully disclosed in pending Ser. No. 203,000, filed June 6, 1988. PCR has been automated; PCR instruments are disclosed in pending Ser. No. 899,061, filed Aug. 22, 1986, which is a CIP of pending Ser. No. 833,368, filed Feb. 25, 1986, now abandoned. Methods for the structure-independent amplification of DNA by PCR utilizing the structure-destabilizing base analog 7-deazaguanine are disclosed in pending U.S. Ser. No. 248,556, filed Sept. 23, 1988, and are especially useful in the practice of the present method. Methods for generating single-stranded DNA by a process termed asymmetric PCR are disclosed in pending U.S. Ser. No. 248,896, filed Sept. 23, 1988, and are especially useful in conjunction with the present method. The disclosures of these related patents and applications are incorporated herein by reference.

Prior to the present invention however, Taq DNA polymerase had not been used in DNA sequencing methods. Taq DNA polymerase exhibits high processivity, a rapid rate of incorporation, and ability to utilize nucleotide analogs to terminate chain extension and to resolve gel compressions. These properties of Taq DNA polymerase are similar to those of a chemically modified bacteriophage T7 DNA polymerase recently decribed by Tabor et al., 1987, *Proc. Natl. Acad. Sci. USA* 84:4767-4771. In contrast to T7 DNA polymerase, however, Taq DNA polymerase is a single-chain enzyme which is highly thermostable, as described by Gelfand et al., European Patent Publication 258,017. Because Taq polymerase has no detectible 3'-5'-exonuclease activity, and because the misincorporation rate is high unless certain dNTP and ddNTP concentrations are used, Taq polymerase has not previously been used for sequencing. The present invention provides efficient protocols for DNA sequencing with Taq DNA polymerase, which can also be used for direct sequencing of PCR-amplified DNA.

SUMMARY OF THE INVENTION

The present invention provides an improved dideoxynucleotide method for determining the nucleotide sequence of a nucleic acid. This improved method involves utilization of the DNA polymerase from *Thermus aquaticus*, called Taq polymerase, for the extension of the primers used in the method. The method of the invention is especially preferred when practiced with single stranded DNA generated by a modified or asymmetric polymerase chain reaction to produce single stranded DNA.

The present method offers significant advantages over known sequencing methods. Many of these advantages arise out of special attributes of Taq DNA polymerase, which will not function properly in dideoxy sequencing protocols designed for the Klenow fragment of *E. coli* DNA polymerase I, reverse transcriptase, or a modified form of T7 DNA polymerase. However, using the method of the present invention, one can generate sequence information with Taq polymerase in a manner not possible with any other known protocol.

For instance, the sequencing reaction of the present method can be practiced over a broad range of temperatures, whereas prior art methods were inoperable at temperatures much higher than 50° C. However, at temperatures of 50° C., many single stranded DNAs can form secondary structure, such as a hairpin loop, that can seriously interfere with a dideoxy sequencing protocol, both through improper termination in the extension reaction and through the generation of aberrant migration patterns on sequencing gels. The ability to conduct the extension reaction at a higher temperature, i.e., 70° C., as provided by the present method, results in a significant improvement in sequencing results with DNA that contains such secondary structure, because high temperature destabilizes secondary structure. The ability to use high temperatures with the present invention also results in increased primer specificity, which, in turn, provides cleaner (less background) and more readable sequence information.

The present method also provides better sequencing results because of the ability to utilize structure-destabilizing base analogs such as 7-deazaguanine in the method. This analog can be used to prevent Hoogsteen bond formation in G+C-rich DNA, which, if not prevented, causes compressions in the DNA and aberrant migration patterns of DNA strands on sequencing gels.

Another important advantage of the present method is the ability to generate sequence information over a long segment of nucleotides in a single sequencing reaction (which, as described below, is really 4 different reactions, one for each nucleotide: A, G, C, and T). Taq polymerase is fast and very processive, and products can be generated by the present method that yield signals of uniform intensity, whether the products are short (within 30 nucleotides of the primer) or long (over 1000 nucleotides from the primer). Nor is this advantage limited to sequence determination by the use of autoradiography. Instead, the nature of the generation of extension products in the present method makes possible, for the first time, an automated DNA sequencing instrument capable of determining over 1000 bases of nucleotide sequence in a single sequencing reaction, independent of the method used for detecting extension products. Prior to the present invention, DNA sequencing instruments produced, at best, less than 600 bases of sequence per sequencing reaction.

Another important aspect of the present invention has an even greater impact on DNA sequencing instrumentation. The PCR process has been automated, and asymmetric PCR can be used for generating a single stranded DNA template for sequencing. The Taq polymerase is preferred for PCR, but prior to the present invention, not preferred for DNA sequencing. With the advent of the present invention, however, generation of template for sequencing and determination of sequence can be carried out in a single automated process. The present invention also relates to certain kits and buffers suitable for use in both PCR and the present method.

BRIEF DESCRIPTION OF THE FIGURES

FIG. 3 shows an autoradiograph of a polyacrylamide-urea gel on which are compared the extension products from (A) an M13-based single-stranded template, and (B) an asymmetric PCR template of the same sequence. The sequencing of the M13 clone was carried out as described in the accompanying Examples using a [³²P]-labeled primer. The asymmetric amplification and subsequent sequencing were performed as described, and all extension products were resolved on a buffer-gradient sequencing gel. Reaction sets were loaded: G, A, T, C.

DETAILED DESCRIPTION OF THE INVENTION

Figures 1A, 1B, 1C:
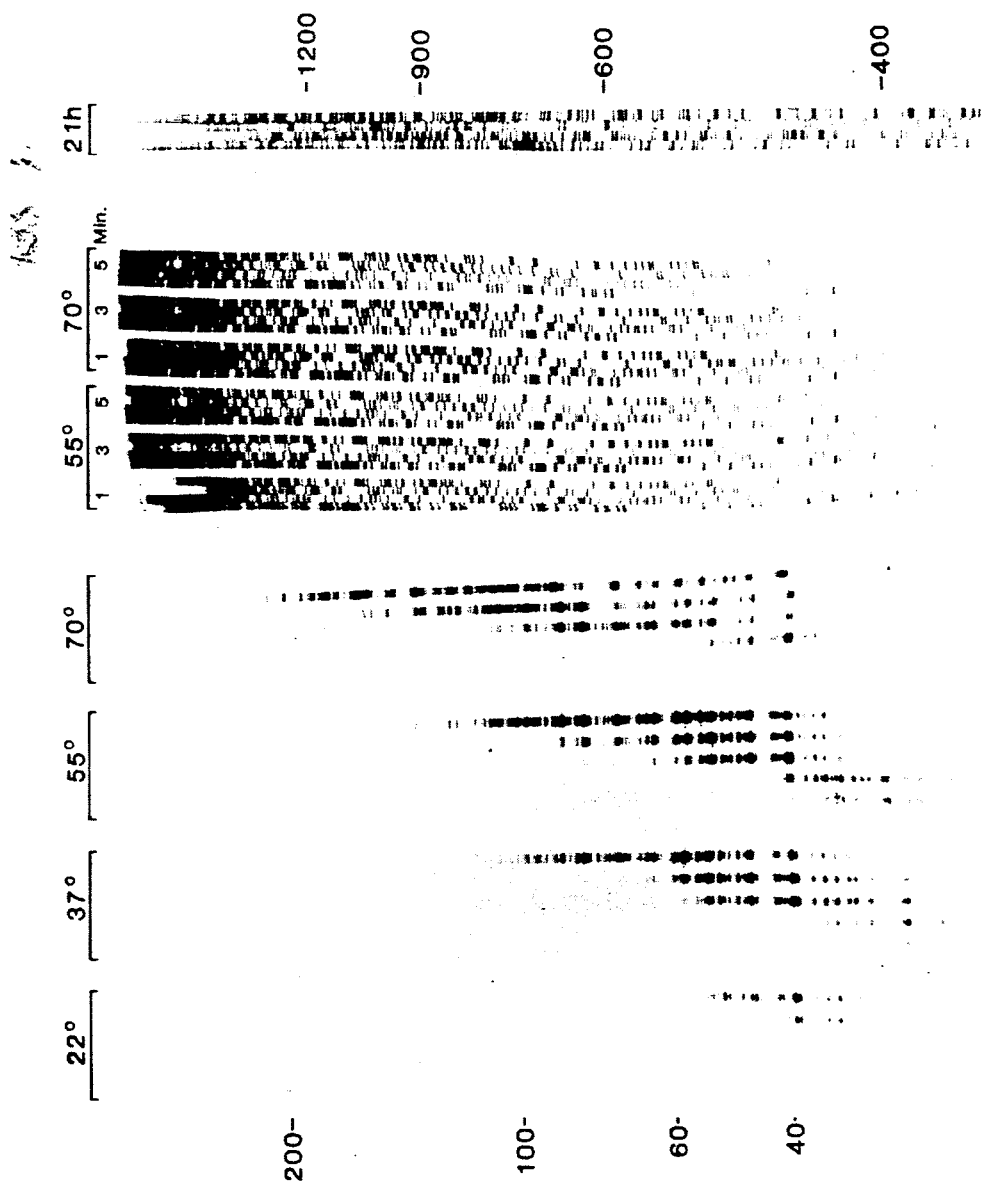
FIG. 1 shows autoradiographs of polyacrylamide-urea gels exhibiting the products of (A) labeling reactions, (B) sequencing (extension-termination) reactions performed at various temperatures, and (C) sequencing reaction products resolved during extended electrophoresis. The labeling reactions were performed as described in Example 4. The reactions were brought up to temperature before the addition of the enzyme. Aliquots were removed at 0.5, 1, 3, 5, 7, and 10 minutes. The extension-termination reactions were performed as described. All reactions were stopped with formamide-EDTA stop solution, denatured at 80° C. for 3 minutes, and resolved on a buffer-gradient sequencing gel (described by Biggin et al., 1983, *Proc. Natl. Acad. Sci. USA* 80:3963-3965). Extended electrophesis (C) was performed on the products of a 70° C./3 minute extension-termination sequencing reaction. Samples were run at 15 W for 21 hours on a 18 cm ×50 cm ×0.4 mm. 7% acrylamide gel (24:1 cross-linking) with 7 M urea and 1X TBE. Markers indicate the distance in nucleotides from the beginning of the primer. All sequencing reaction sets are loaded: G, A, T, C.

The Sanger and other dideoxynucleoside DNA sequencing protocols involve a series of four reactions, each of which involves the template-dependent extension of an oligonucleotide primer annealed to the nucleic acid to be sequenced, the template. The extension reaction is catalyzed by an agent for template-dependent polymerization. The template DNA is single stranded, so the primer can anneal to the template, and each of the four extension reactions is carried out in the presence of the four dideoxynucleoside-5'-triphosphates (dATP, dCTP, dGTP, and TTP) or in a similar mixture containing one or more natural or synthetic analogs of dATP, dCTP, dGTP, or TTP and one dideoxynucleoside-5'-triphosphate (ddNTP). Incorporation of a ddNTP terminates the extension reaction, and the ddNTP concentration can be adjusted so that the reaction generates molecules of a broad range of chain lengths. The four separate reactions are utilized so that in one reaction all extension products end with ddATP, in another with ddCTP, in another with ddGTP, and in the fourth with ddTTP. Through use of labeled primers, dNTPs, or ddNTPs, the products of the extension reaction can be detected. Separation of the products by size, i.e., on a sequencing gel in side-by-side lanes, and visualization or other detection of the extension reaction products allows the sequence of the template to be determined.

Prior to the present invention, the extension products in dideoxy sequencing methods were generated by agents for polymerization such as the Klenow fragment of *E. coli* DNA polymerase I, reverse transcriptase, or a modified T7 DNA polymerase. The present invention provides a significantly improved method for dideoxynucleotide sequencing that utilizes the DNA polymerase from *Thermus aquaticus*, Taq polymerase, to catalyze the extension reaction.

The present invention provides convenient and efficient methods for sequencing DNA with Taq DNA polymerase. The methods work equally well with either 5'-labeled primers or by incorporation of label in a two-step reaction protocol. Both methods of incorporating label have been used to generate DNA sequencing ladders that are characteristically free of background bands or noticeable enzyme idiosyncrasies, uniform in intensity, and readable over long distances. The present protocols also gave very clean results in sequencing alkali-denatured double stranded DNA templates.

The advantages of the present method will make Taq DNA polymerase the polymerase of choice for most sequencing applications. Sequencing results obtained using the present method were far superior to those obtained using either Klenow or AMV reverse transcriptase methodologies and were better than the results obtained using a method for sequencing with modified T7 DNA polymerase. One reason for these superior results is that, unlike any of these polymerases, Taq DNA polymerase works over a broad temperature optimum centered around 75° C. Regions of DNA secondary structure (hairpins) are commonly encountered and can strongly hinder a DNA polymerase and cause premature termination of the primer extension reaction. This result is observed as bands across all four sequencing lanes on sequencing gels and is cause for failure no matter how extension products are detected. Other structures can interfere in sequencing and are common in high G+C DNA as a result of compression through Hoogsteen bond formation, but can also occur in DNA with no apparent abnormalities. The ability of Taq DNA polymerase to operate at high temperature and low salt allows heat-destablization of hairpins during the sequencing reaction, permitting the enzyme to read through such structures. The concomitant use in the present method of a structure-destabilizing dGTP analog, such as 7-deaza-2'-deoxyguanosine-5'-triphosphate (c⁷dGTP), yields sequencing products from such difficult to sequence DNA that were fully resolved upon electrophoresis (see also copending U.S. Ser. No. 248,556, filed Sept. 23, 1988).

Absence of background bands and uniform intensity of the radioactive fragments are benefits provided by the present method. Another benefit is due to the fact that Taq DNA polymerase is very processive. Within two minutes at 70° C., the Taq enzyme can replicate an entire 7.25 kb template. This equals a turnover rate in excess of 60 nucleotides per second. Taq DNA polymerase also has significant activity at lower temperatures with calculated turnover rates of 24, 1.5, and 0.25 nucleotides per second at 55° C., 37° C. and 22° C., respectively. In the absence of ddNTPs, a Taq DNA polymerase extension reaction, at 70° C. and at a substantial substrate excess (0.1:1 molar ratio of polymerase to primer/template), will extend most initiated primers completely prior to reinitiation on new substrate. The extension rate is relatively independent of enzyme concentration and demonstrates that Taq DNA polymerase has high processivity. Taq DNA polymerase also has very little if any proofreading activity.

These properties of Taq enzyme make the present method preferred over other sequencing methods. Polymerase pausing and premature termination of chain extension at sequences with secondary structure is reduced and discrimination against dideoxynucleotide analogs is diminished by the present method. These benefits make the invention preferred for use in automated sequencing instruments. Ironically, however, one of the beneficial properties of Taq polymerase for sequencing, the absence of significant Taq-associated 3'→5'-exonuclease activity, undoubtedly prevented the development of Taq polymerase sequencing methods even after the purification of the enzyme by Gelfand et al. (European Patent Publication No. EPO 258,017). This is because absence of a 3'→5'-exonuclease activity results in a failure to remove misincorporated bases and results in chain termination. Misincorporation occurs at very low and generally unbalanced nucleotide concentrations typically used in prior art methods. The present inventors discovered that the rate is enhanced unacceptably for sequencing when one or more of the dNTPs are well below Km and/or when the concentration of one dNTP is very low relative to the other dNTPs. The present inventors also discovered that conditions which favor high fidelity and catalytic efficiency over long distances reactions are similar concentrations of each of the four dNTPs and $\geq 10$ $\mu$M for each dNTP.

The chain extension reaction conditions of the present sequencing method are especially preferred when carried out in a buffer compatible with PCR, as is discussed more fully below. The buffer (described by Saiki et al., 1988, Science 239:487-494) for Taq polymerase PCR reactions (50 mM KCl; 10 mM Tris-HCl, pH 8.4; 2.5 mM MgCl$_2$; 200 $\mu$M of each dNTP; and 200 $\mu$g/mL of gelatin) was accordingly modified by the present inventors for DNA sequencing. The PCR buffer described by Saiki et al. contains KCl. For purposes of the present method, however, the best extensions occur in the absence of KCl. At 50 mM KCl there was slight inhibition of enzyme activity, and at $\geq 75$ mM KCl, the activity of Taq DNA polymerase was significantly inhibited in the present method. The presence or absence of gelatin, which acts as an enzyme stabilizer in PCR reactions, did not affect the sequencing reactions per se; however, gelatin can cause distortions during electrophoresis. Addition of non-ionic detergents to the enzyme dilution buffer (final concentration of detergent in the sequencing reaction: 0.05% Tween 20 and 0.05% NP40) stimulated the activity of the Taq DNA polymerase and reduced the background caused by false terminations from the enzyme.

Taq DNA polymerase requires free magnesium ion; the concentration of magnesium ion should generally be at least 0.8 mM above that of the dNTPs and ddNTPs present in the sequencing reaction of the present invention. Thus, the preferred PCR buffer for use in conjunction with the present invention does not contain KCl, but does contain 0.05% Tween 20, 0.05% NP40, 3 mM (or higher) MgCl$_2$, in a buffer, 10 mMTris-HCl is preferred, at pH 8.0 to 8.5. The reaction mixtures also contain primer, template, Taq polymerase, dNTPs, and ddNTPs.

The present method can tolerate a wide variety of nucleotide concentrations, especially if each dNTP is present at concentrations greater than 10 $\mu$M. However, ddNTPs are expensive, and must be present in the extension reaction at a ratio to the corresponding dNTP for generation of meaningful sequence information. Consequently, lower dNTP concentrations are preferred for any dideoxy sequencing method. At concentrations of less than 5 $\mu$M in each of four dNTPs, and when the concentration of one dNTP was low relative to the other dNTPs, a high background of incorrect termination products was seen due to misincorporation of both dNTPs and ddNTPs.

Thus, the optimum concentration for each ddNTP was empirically determined in a solution containing of all four dNTPs, each present at 10 $\mu$M. Taq DNA polymerase incorporated the four ddNTPs with varying efficiency, and much less efficiently than the corresponding dNTPs. Ratios that generated optimal distributions of chain termination products were: dGTP:ddGTP (1:6), dATP:ddATP (1:32), TTP:ddTTP (1:48), and dCTP:ddCTP (1:16).

Taq DNA polymerase concentration was varied between 1 and 20 units per set of four reactions containing 0.2 pmol of single stranded DNA template, 0.5 pmol of primer, and the dNTP:ddNTP concentrations described above. The amount of extension products synthesized increased up to 10 units of polymerase per reaction set. At this concentration of reagents, ten units of Taq DNA polymerase represented approximately a 2.5-fold molar excess of enzyme over template-primer; however, a one:one ratio of Taq polymerase: template-primer is less costly and works well.

The present invention also encompasses a variety of methods for incorporating labeled nucleotide during the sequencing reaction. One popular method involves the use of a labeled primer in the sequencing (chain extension and termination) reactions. Another method involves incorporation of a labeled nucleotide into the extending primer. A Klenow-type protocol, where one labeled nucleotide is present at low concentration relative to the other three during primer extension, however, will not work with Taq polymerase due to misincorporation of dNTPs and ddNTPs. The apparent Km values for each of the four dNTPs is between 10 $\mu$M and 20 $\mu$M. When the concentration of one labeled nucleotide, either {$\alpha$-[$^{35}$S]thio}dATP, or {$\alpha$-[$^{35}$S]thio}dCTP, was significantly below Km (i.e., about 0.5 to 1 $\mu$M), ddNTPs present at 80-500 $\mu$M were inappropriately incorporated at high frequency with Taq Polymerase. Concentrations higher than 1 $\mu$M for an [$\alpha$-$^{35}$S]-labeled dNTP are not practical. Also, because the Taq enzyme apparently lacks 3'→5'-exonuclease (proofreading) activity, misincorporated dNTPs induce chain termination.

To circumvent these problems and realize the full benefits of dideoxy sequencing with Taq polymerase, the present invention provides a two-step procedure involving an initial low temperature labeling step using uniformly low concentrations of all four dNTPs (one of which is labeled) followed by the sequencing reaction step in the presence of ddNTPs and higher dNTP concentrations. The sequencing reaction can be performed at higher temperatures to achieve superior results. To obtain sequence data in the region next to the primer utilizing this labeling procedure, it is preferred to use both low temperature and limiting dNTP concentrations to generate an array of radioactive extension products ranging in size from a few to greater than 100 nucleotides in length. Minimum concentrations of 0.5 $\mu$M for each labeled dNTP are preferred in this step to generate easily readable signals from an overnight exposure, and increasing the concentration of one unlabeled dNTP to 1.0 $\mu$M make the signals very clear. This benefit is seen regardless of which dNTP is increased, but increasing more than one is not necessary.

After the labeled nucleotide is incorporated to readable levels, the sequencing reaction is initiated by the addition of balanced dNTPs ($\geq 10$ $\mu$M each) and ddNTPs. During the sequencing reactions, temperature increase and higher dNTP concentrations ensure maximum processivity and fidelity with the present method. Sequencing reactions work well in a broad temperature range. The reactions performed at 55° C. occurred at a slower rate, consistent with the extension rates described above, but there was no detectable difference in fidelity as compared with 70° C. Under these conditions, there was remarkable uniformity in the band intensities, and no detectable idiosyncratic band patterns. In addition, the same reaction conditions cover both short and long gel runs. DNA sequence information in excess of 1000 nucleotides from the priming site can be generated using the present method, as shown in FIG. 1(c).

Figure 2:
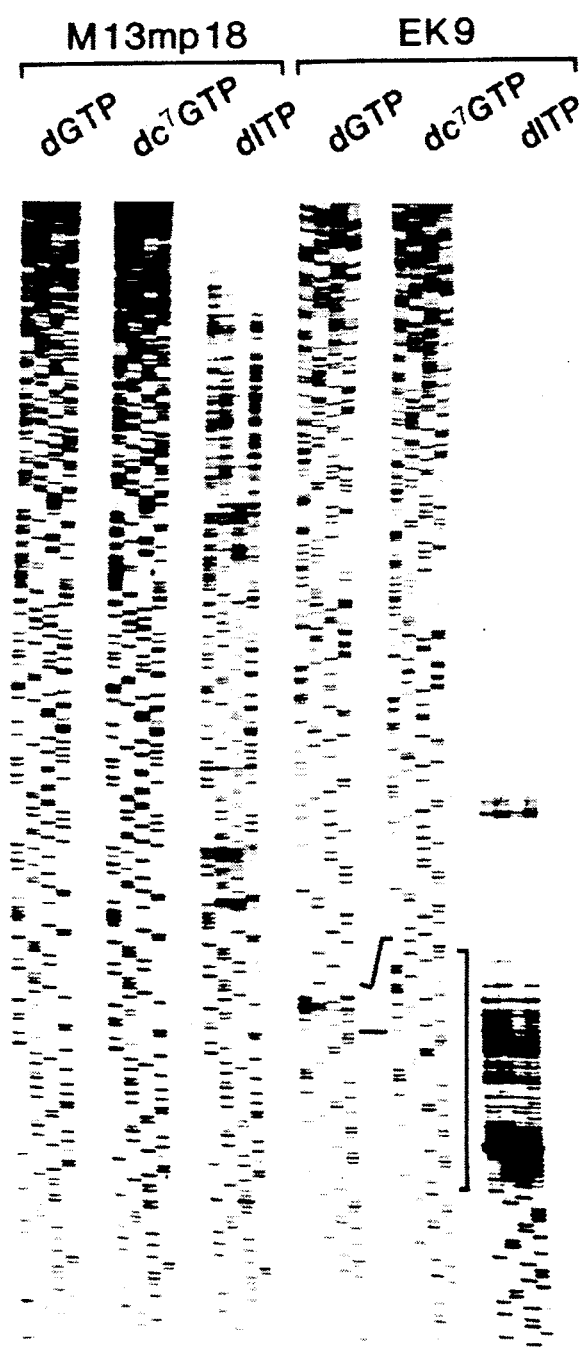
FIG. 2 shows an autoradiograph of a polyacrylamide-urea gel comparing extension products generated with base analogs. The effects of replacing dGTP with c⁷dGTP (7-deaza-2'-deoxyguanosine-5'-triphosphate is abbreviated in the text as c⁷dGTP but is abbreviated in the Figure as dc⁷GTP) or dITP are shown in sequencing reactions performed on M13:mp18 single-stranded DNA or on a partially palindromic clone, EK9. Lanes are loaded: G, A, T, C. Lines between the EK9 dGTP and c⁷dGTP reaction sets align the same positions upstream and downstream of the compressed region. The bracket indicates the limits of the palindrome. The correct sequence of the region is: 5'-CCATGT GACCCTGCCCGACTTCGACG GGAATTCCCGTC"GAAGTCGGGCAGGGT CACC"ATA-3'. The complementary bases are underlined and the bases compressed in the dGTP reactions are in quotes.

The present method can also be carried out using the base analog 7-deaza-2'-deoxyguanosine-5'-triphosphate ($c^7dGTP$) and high temperature to sequence through G+C-rich DNA and to eliminate band compressions. Band compressions resulting from abnormal gel migration of certain sequences are frequently encountered with G+C-rich DNA templates and occur even in cloned DNA sequences with no apparent abnormality in base composition. Such compressions can result in inconclusive or error-prone reading of sequencing gels. Substitution of dGTP with dITP or $c^7dGTP$, has been somewhat useful in resolving compression artifacts in known sequencing protocols. Incorporation of such nucleotide triphosphate analogs by Taq polymerase in the present method was investigated using either an M13:mp18 template or a G+C-rich, strong dyad symmetry-containing insert cloned into M13, as shown in FIG. 2. Taq DNA polymerase incorporated $c^7dGTP$ with essentially the same kinetics as dGTP, and a combination of high reaction temperature and $c^7dGTP$ is very efficient for resolving difficult sequences.

In contrast, inosine-containing reactions required a 4-fold higher level of dITP as compared to dGTP, the labeling reaction needed 4 minutes, and the ratio of ddGTP to dITP was reduced 20-fold compared to dGTP. Because deoxyinosine-5-triphosphate (dITP) base-pairs promiscuously, frequent chain termination at regions of secondary structure occur with dITP, which is therefore not preferred for purposes of the present invention. Terminations caused by inosine result both from a higher rate of misincorporation with dITP as compared to the other dNTPs and from the fact that Taq DNA polymerase lacks the necessary $3' \to 5'$-exonuclease activity for editing misincorporated bases. Terminations induced by dITP are greatly reduced if the reactions are initiated at 70° C.

Development of a procedure for direct sequencing of PCR products has been needed since the inception of the PCR technique. The remarkable DNA sequencing results obtained by the present invention, coupled with the compatibility of the present method with PCR, makes the present method the ideal method for directly analyzing PCR products (see FIG. 3). Sequence analysis of cloned PCR products by the present method suggests that the fidelity for PCR using 50-200 μM of each dNTP is quite respectable (approximately one mistake in 4000 nucleotides sequenced following 35 cycles of PCR and cloning of the PCR products) and is comparable with that observed using other DNA polymerases for PCR. Additionally, most misincorporation errors that may occur in the PCR reaction will cause chaintermination, thus preventing amplification of defective molecules.

The present method is especially preferred for use with asymmetric PCR reactions using primers at concentrations designed to first amplify and then generate single stranded DNA (ssDNA) from any insert. Generation of single stranded DNA by a process termed asymmetric PCR is described in pending U.S. patent application Ser. No. 248,896, filed Sept. 23, 1988. This embodiment of the invention was illustrated by cloning DNA into the M13/pUC-lacZ polylinker and generating ssDNA by asymmetric PCR. Asymmetric PCR was performed, as described in the accompanying examples, with one of the oligonucleotide primers present in a 100-fold greater concentration than the other, so that one of the two PCR primers was depleted during the early thermal cycles. The reaction generated single stranded product from the remaining primer.

Sequencing of asymmetric PCR-generated templates by the present method did not require purification of the product. Based on an estimated yield of 1 μg of single stranded product, one-third to one-half of the 2 nmol of each dNTP initially added are used up during the PCR cycles. In addition, the stability of the dNTPs during PCR was determined to be approximately 50% after 60 cycles of PCR. Accordingly, the termination mixes used in the present method are formulated to boost the dNTPs to a final concentration of about 10 μM or higher in the sequencing reaction, to supply specific ddNTPs at appropriate concentrations as determined above, and to provide additional DNA polymerase. A [$^{32}$P]-labeled sequencing primer can be used to avoid purifying the PCR product and to simplify the sequencing protocol to a single extension/termination step. It is obvious that a fluorescently-labeled sequencing primer(s) could also be used in the present methods; the products can then be analyzed on an automated DNA sequencing instrument.

DNA sequence obtained with Taq DNA polymerase using either an asymmetric PCR-generated template or the same DNA insert cloned in M13:mp18 as template was compared. The resulting sequence ladders showed the clarity and uniformity of signal characteristic of Taq-generated sequences. Any degradation of enzyme or dNTPs that may have occurred during the PCR thermal cycling did not seem to affect the generation of clean sequence data. Synthesis of single-stranded DNA template during 35 cycles of PCR was largely independent of the initial DNA concentration. Asymmetric PCR reactions performed using either 0.1 to 100 ng of M13:mp10 ssDNA, or 10 μL of an M13 phage plaque picked directly into 100 μl of water, sequenced equivalently using the method of the invention.

Although the present invention is illustrated below by sequencing inserts cloned into M13/pUC-based vectors, the method is applicable to direct sequencing of clones in lambda phage or any other cloning vector. Some variability in the ssDNA yield of the asymmetric PCR reaction has been observed for different primer pairs and ratios, and the reaction conditions for each amplification system will need to be adjusted to give the optimum results for a particular primer pair and template nucleic acid. The PCR dNTP concentrations may also need to be varied for products of different sizes and/or amplification efficiencies. Additionally, some investigators have increased the homogeneity of PCR products from genomic DNA by electrophoretic separation and reamplification of eluate from a selected gel slice. The present sequencing method is easily applied to this "secondary" form of PCR. Direct sequencing of PCR products from DNA by any method produces a "consensus" sequence; those bases which occur at a given position in the majority of the molecules will be the most visible on an autoradiograph and any low-frequency errors will be undetectable. In such a PCR-coupled embodiment of the present invention, the resulting sequence data will be only as clean as the amplified product. Heterogeneous products will naturally produce mixed ladders.

Because Taq DNA polymerase is very useful for PCR, the present invention makes possible the coupling of template preparation by PCR with direct sequencing. This advantage is significant in that it is now possible, by virtue of the present method, to automate both DNA template preparation by PCR and performance of the sequencing reactions in a manner compatible with current partially automated DNA sequencing instruments.

Those skilled in the art recognize that the present method can be used in a variety of contexts where determination of DNA sequence information is desired. The following examples are provided merely to illustrate the invention and not to limit the scope of the accompanying claims. Example 4 presents a preferred embodiment of the present invention.

EXAMPLE 1

Annealing, Labeling, and Extension-Termination Reactions

The materials used in the procedures described below were obtained as follows. Polynucleotide kinase from T4-infected *E. coli* cells was purchased from Pharmacia. Taq DNA polymerase, a single subunit enzyme, was purified from *Thermus aquaticus*, strain YT-1 (ATCC #2543). More recently, Taq DNA polymerase was purchased from Perkin Elmer-Cetus Instruments. The polymerase (5-80 units/$\mu$L) was stored at $-20°$ C. in 20 mM Tris-HCl, pH 8.0; 100 mM KCl; 0.1 mM EDTA; 1 mM DTT; 200 $\mu$g/mL autoclaved gelatin; 0.5% NP40; 0.5% Tween-20; and 50% glycerol. The enzyme has an approximate specific activity of 200,000 units/mg, with one unit corresponding to 10 nmol of product synthesized in 30 minutes using activated salmon sperm DNA. 2'-deoxy and 2',3'-dideoxynucleotide-5'-triphosphates (dNTPs and ddNTPs) were obtained from Pharmacia. 7-deaza-2'-deoxyguanosine-5'-triphosphate (c$^7$dGTP) was from Boehringer Mannheim. $\{\alpha$-[$^{35}$S]thio$\}$dATP (650 Ci/mmol) was from Amersham, and $\gamma$-[$^{32}$P]ATP was from New England Nuclear. Oligonucleotide primers for sequencing were synthesized on a Biosearch 8700 DNA Synthesizer using cyanoethyl phosphoramidite chemistry. Oligonucleotide primers were 5'-end labeled ($3\times10^6$ cpm/pmol) with $\gamma$-[$^{32}$P]ATP and T4 polynucleotide kinase (Maxam and Gilbert, 1980, *Methods Enz.*, 65:499-560). Single stranded M13 DNA templates were prepared as described by Zinder et al., 1982, *Gene*, 19:1-10.

Single annealing and labeling reactions were performed for each set of four sequencing reactions in 1.5 mL microfuge tubes. The annealing mixture contained 5 $\mu$L of oligonucleotide primer (0.1 pmol/$\mu$L) in 6 x Taq Sequencing Buffer (TSB, 10 mM MgCl$_2$ and 10 mM Tris-HCl, pH 8.0, at room temperature) and 5 $\mu$L of template DNA (0.05 to 0.5 pmol). The mixture was heated in a boiling water bath for three minutes, incubated at 42° C. for 20 minutes, cooled to room temperature, and briefly spun to collect the fluid at the bottom of the tube.

To the 10 $\mu$L annealing reaction were added 2 $\mu$L of labeling mix (10 $\mu$M dGTP, 5 $\mu$M dCTP, and 5 $\mu$M TTP in 10 mM Tris-HCl, pH 8.0), 2 $\mu$L of $\{\alpha$-[$^{35}$S]thio$\}$dATP (5 $\mu$M after 3$\times$ dilution in 10 mM Tris-HCl, pH 8.0), 2 $\mu$L of Taq DNA polymerase (5 units/$\mu$L in dilution buffer: 10 mM Tris-HCl, pH 8.0; 0.5% Tween 20; and 0.5% NP40), and 4 $\mu$L H$_2$O. The labeling reaction was incubated for one minute at 37° C. For sequencing with 5'-labeled primers, the addition of $\{\alpha$-[$^{35}$S]thio$\}$dNTP, labeling mix, and the labeling reaction were omitted, and the volume was made up with 10 mM Tris-HCl, pH 8.0.

Four separate sequencing (extension-termination) reactions were performed in 96-well microtiter plates (Falcon #3911) for each labeled template using concentrated deoxy/dideoxy termination mixes as follows: "G-mix" (30 $\mu$M in each dNTP, 0.25 mM ddGTP, and 0.37 mM MgCl$_2$); "A-mix" (30 $\mu$M in each dNTP, 1.0 mM ddATP, and 1.12 mM MgCl$_2$); "T-mix" (30 $\mu$M in each dNTP, 1.5 mM ddTTP, and 1.62 mM MgCl$_2$); and "C-mix" (30 $\mu$M in each dNTP, 0.5 mM ddCTP, and 0.62 mM MgCl$^2$). Four $\mu$L aliquots from the labeling reactions were added at room temperature to wells containing 2 $\mu$L of the appropriate termination mix. Reactions were overlaid with 10 $\mu$L of mineral oil to prevent evaporation and then incubated at 70° C. for one to three minutes. Reactions were stopped by the addition of 2 $\mu$L of 95% deionized formamide containing 0.1% bromophenol blue, 0.1% xylene cyanol, and 10 mM EDTA, pH 7.0. Samples were heated at 80° C. for three minutes before loading 1 to 2 $\mu$L onto a buffer-gradient sequencing gel, as described by Biggin et al., *Proc. Natl. Acad. Sci. USA* 80:3963-3965. Results are shown in FIG. 1.

EXAMPLE 2

Asymmetric Polymerase Chain Reactions

This example describes how DNA can be generated for sequencing by the present method. The template for asymmetric PCR reactions was single stranded M13:mp10 DNA containing a 400 base insert in the EcoRI site of the polylinker. Oligonucleotides (20-mers) were synthesized to flank the polylinker immediately outside of the universal "-20" and "Reverse" sequencing primer binding sites, and these primers were designated RG05 (5'AGGGTTTTCCCAGTCACGAC3') and RG02 (5'GTGTGGAATTGTGAGCGGAT3'), respectively. Each PCR reaction contained 20 pmol of one primer and 0.2 pmol of the other primer, 20 $\mu$M of each dNTP, 1 to 10 ng of DNA, 1X modified PCR buffer (10 mM Tris-HCl, pH 8.0; 3.0 mM MgCl$_2$, and 0.05% of each of Tween 20 and NP40), and 2.5 units of Taq DNA polymerase in a total volume of 100 $\mu$L. The reactions were overlaid with 75 $\mu$L of mineral oil to prevent evaporation.

Reactions were performed in 0.5 mL microcentrifuge tubes using the Perkin Elmer-Cetus Thermal Cycler. The programmed thermal profile was initiated with a denaturation at 93° C. for 30 seconds, cooled for primer annealing at 50° C. for one minute, heated up to the 72° C. extension temperature over the course of 1.5 minutes, and held at 72° C. for one minute to ensure completed extension. This profile was repeated for 35 cycles, and the final 72° C. incubation was extended to 10 minutes.

EXAMPLE 3

Sequencing of PCR Products

Aliquots of PCR reactions were directly incorporated into dideoxy chain-termination sequencing reactions. A set of four, base-specific chain-termination sequencing mixes was made up, each in 1X modified PCR Buffer and 20 μM of each dNTP. The individual mixes contained 250 μM ddGTP, 1.28 mM ddATP, 1.92 mM ddTTP, or 640 μM ddCTP. For each PCR product to be sequenced, four wells on a 96-well microtiter plate were labeled "G", "A", "T", or "C", and each well received 2.5 μL of the appropriate sequencing termination mix. A 20 μL aliquot of each PCR reaction was removed to a 1.5 mL microcentrifuge tube and mixed with 0.5 μL of fresh Taq DNA polymerase (48 units/μL), 1 μL of the appropriate [$^{32}$P]-labeled M13 forward or reverse sequencing primer (5'GTAAAACGACGGCCAGT3' and 5'AACAGCTATGACCATG3', respectively, 1.2 pmol per μL) and 10.5 μL of 1X modified PCR buffer. The PCR/primer preparation was immediately distributed in 7.5 μL aliquots into the wells containing the termination mixes and mixed with the pipettor. Samples were overlaid with 10 μL of mineral oil, and the plate was spun to collect the reaction mixture and to distribute the oil across the wells in an even layer. The reactions were incubated at 70° C. for two minutes and stopped by the addition of 4 μL of 91% formamide with 20 mM EDTA pH 8.0, and 0.05% each of xylene cyanol and bromophenol blue. 5 μL aliquots of these reactions were heated to 75° C. for five minutes, and 1 to 2 μL were loaded on a buffer gradient sequencing gel. The results are shown in FIG. 3.

EXAMPLE 4

Preferred Sequencing Protocol

A. ANNEALING TEMPLATE AND PRIMER

Combine in a 1.5 ml microcentrifuge tube: 5 μL of template DNA (0.5 pmol); 1 μL of primer (0.5 pmol); and 4 μL of 5X Sequencing Buffer. The total volume should be 10 μL; if a smaller volume of DNA is used, make up the difference with distilled water. Heat the tube at 70° C. for 3 minutes, then at 42° C. for 10 minutes.

B. LABELING REACTION

Dilute the Taq DNA polymerase enzyme 1:10 in Enzyme Dilution Buffer to 5 U/μL; keep on ice. To the annealed template/primer add the following: 2 μL of Labeling Mix (dGTP or c$^7$dGTP); 1 μL of {α-[$^{35}$S]thio}dATP (>600 Ci/mmol; diluted to 10 μM in 10 mM Tris-HCl, pH 8.5); 5 μL of distilled water; and 2 μL of diluted Taq DNA polymerase (5 U/μL). Vortex briefly to mix, collect by spinning the tube in a microfuge, and incubate at 37° C. for 2 minutes.

Note that the c$^7$dGTP Labeling Mix should be used if c$^7$dGTP will be used in the sequencing reactions. Use of c$^7$dGTP is recommended for resolving sequences which cause compressions on the gel. Termination Mixes should be aliquoted into the microtiter plate wells prior to starting the labeling reaction. If labeled primers are to be used for sequencing, the {α-[$^{35}$S]thio}dATP, Labeling Mix, and the labeling reaction incubation are omitted, and the volume is brought to 20 μl with 10 mM Tris-HCl, pH 8.5.

C. TERMINATION REACTIONS

The sequencing termination reactions may be carried out in a microtiter plate (Falcon #3911), using 4 wells per template/primer, labeled G, A, T, and C. Place 2 μL of the ddGTP Termination Mix in the well labeled G. Similarly, place 2 μL of the ddATP, ddTTP, and ddCTP Termination Mixes in the appropriately labeled wells. Note that the c$^7$dGTP Termination Mixes should be used if c$^7$dGTP was used in the labeling reaction.

Immediately upon completion of the labeling reaction, transfer 4 μL aliquots to each of the four wells labeled G, A, T, and C. Place the drops on the sides of the wells, and allow them to slide down to mix with the Termination Mixes. When all wells for all reactions are filled, briefly spin the microtiter plate to ensure that mixing of the labeling reactions with the Termination Mixes is complete.

Incubate the microtiter plate, at 70° C. for 2 minutes, using a heat block which will contact the well bottoms. This time is sufficient to generate extension products greater than 1500 bp in length. Longer times lead to excessive evaporation.

D. STOPPING REACTIONS

Remove the reactions from the heat block and place at room temperature. Add 2 μL of Stop Solution to the side of each well. Briefly spin the microtiter plate to mix the Stop Solution with the reactions. Samples may be stored covered at −20° C. for up to 7 days with minimal degradation.

Immediately prior to loading samples on the gel, heat to 70° C. for 4 minutes. Load 1 to 2 μL per sample in each lane.

E. REAGENTS

Taq DNA Polymerase Sequencing Buffer (5× Concentrate) is 50 mM Tris-HCl, pH 8.5; and 30 mM MgCl$_2$.

Enzyme Dilution Buffer is 10 mM Tris-HCl, pH 8.0; 0.5% Tween 20; and 0.5% NP40.

Labeling Mix (c$^7$dGTP) is 10 μM c$^7$dGTP; 5 μM dCTP; and 5 μM TTP.

Labeling Mix (dGTP) is 10 μM dGTP; 5 μM dCTP; and 5 μM TTP.

ddG Termination Mix (for c$^7$dGTP) is 60 μM c$^7$dGTP; 30 μM in each of dATP, TTP, and dCTP; and 180 μM ddGTP.

ddG Termination Mix (for dGTP) is 30 μM in each dNTP and 180 μM ddGTP.

ddA Termination Mix (for c$^7$dGTP) is 60 μM c$^7$dGTP; 30 μM in each of dATP, TTP, dCTP; and 1 mM ddATP.

ddA Termination Mix (for dGTP) is 30 μM in each dNTP and 1 mM ddATP.

ddT Termination Mix (for c$^7$dGTP) is 60 μM c$^7$dGTP; 30 μM in each of dATP, TTP, and dCTP; and 1.5 mM ddTTP.

ddT Termination Mix (for dGTP) is 30 μM in each dNTP and 1.5 mM ddTTP.

ddC Termination Mix (for c$^7$dGTP) is 60 μM c$^7$dGTP; 30 μM in each of dATP, TTP, and dCTP; and 500 μM ddCTP.

ddC Termination Mix (for dGTP) is 30 μM in each dNTP and 500 μM ddCTP.

Taq DNA polymerase enzyme is stored at a concentration of 50 U/μL.

Stop Solution is 95% formamide; 20 μM ESTA; 0.1% bromophenol blue; and 0.1% xylene cyanol.

Other modifications of the embodiments of the invention described above that are obvious to those of ordinary skill in the areas of molecular biology, medical diagnostic technology, biochemistry, and related disciplines are intended to be within the scope of the accompanying claims.

We claim:

1. In a method for determining a nucleotide sequence for a nucleic acid segment by a dideoxynucleoside-5'-triphosphate chain termination procedure, wherein said sequence is determined by extending an oligonucleotide primer in a templatedependent manner in the presence of an agent for polymerization, four dideoxynucleoside- 5'-triphosphates (dNTPs), and a dideoxynucleoside- 5'-triphosphate (ddNTP), the improvement comprising extending said primer in the presence of the agent for polymerization that is *Thermus aquaticus* DNA polymerase.

2. The method of claim 1, wherein said primer is labeled.

3. The method of claim 1, wherein one of the four dNTPs or ddNTP is labeled.

4. The method of claim 1, wherein the four dideoxynucleoside-5'-triphosphates are dATP, dCTP, dGTP, and TTP.

5. The method of claim 1, wherein the four dideoxynucleoside- 5'-triphosphates are dATP, dCTP, $c^7$dGTP, and TTP.

6. The method of claim 1, wherein the four dideoxynucleoside- 5'-triphosphates are dATP, dCTP, dITP, and TTP.

7. The method of claim 1, wherein said nucleic acid segment was produced by an asymmertric polymerase chain reaction.

8. The method of claim 1, wherein said nucleic acid segment was produced by an asymmetric polymerase chain reaction.

9. The method of claim 1, wherein no KCl is present in the reaction mixture.

10. The method of claim 1, wherein the DNA polymerase is present in up to a 2.5 -fold molar excess over the nucleic acid segment.

11. The method of claim 2, wherein said primer is labeled with $^{32}$P, $^{35}$S, or a fluorescent molecule.

12. The method of claim 3, wherein said dNTP or ddNTP is labeled with $^{35}$S, $^{32}$P, or a fluorescent molecule.

13. The method of claim 3, wherein said extension reaction is carried out first at a low temperature and in the presence of three unlabeled dNTPs and one labeled dNTP each present at a concentration of less than 1 µM and then at higher temperatures in higher concentrations of the unlabeled dNTPs.

14. The method of claim 4, wherein said dideoxynucleoside- 5'-triphosphate is ddATP.

15. The method of claim 4, wherein said dideoxynucleoside- 5'-triphosphate is ddCTP.

16. The method of claim 4, wherein said dideoxynucleoside- 5'-triphosphate is ddGTP.

17. The method of claim 4, wherein said dideoxynucleoside- 5'-triphosphate is ddTTP.

18. The method of claim 4, wherein $c^7$dGTP is also present during primer extension.

19. The method of claim 4, wherein each dNTP is present at a concentration of 5 µM to 30 µM.

20. The method of claim 13, wherein the concentration of said labeled dNTP is 0.5 µM and the concentration of each unlabeled dNTP is 1.0 µM during said low temperature extension reaction.

21. The method of claim 14, wherein the dATP:ddATP ratio is 1:32.

22. The method of claim 15, wherein the dCTP:ddCTP ratio is 1:16.

23. The method of claim 16, wherein the dGTP:ddGTP ratio is 1:6.

24. The method of claim 17, wherein the TTP:ddTTP ratio is 1:48.

25. The method of claim 19, wherein the concentration of each dNTP is 10 µM.

26. A kit for determining a nucleotide sequence for a nucleic acid segment by a dideoxynucleoside-5'-triphosphate chain termination procedure, which kit comprises
   (a) a primer for extending, in a template-dependent manner, a nucleic acid comprising a sequence complementary to said nucleic acid segment;
   (b) four deoxyribonucleoside-5'-triphosphates (dNTPs);
   (c) four dideoxyribonucleoside-5'-triphosphates (ddNTPs); and
   (d) Taq polymerase.

27. The kit of claim 26, wherein said dNTPs are dGTP, dATP, TTP, and dCTP, and said ddNTPs are ddGTP, ddATP, ddTTP, and ddCTP.

28. The kit of claim 26 that comprises $c^7$dGTP.

29. The kit of claim 26, wherein said dNTPs are described as a set of four dNTPs selected from the group consisting of:
   dGTP, dATP, dCTP, and TTP;
   $c^7$dGTP, dATP, dCTP, and TTP; and
   dITP, dATP, dCTP, and TTP.

30. The kit of claim 26, wherein said primer hybridizes to an M13 cloning vector and is suitable for sequencing cloned inserts in M13 and/or pUC-based vectors.

31. The kit of claim 27, that comprises:
   (i) a G-termination mix comprising dGTP, dATP, TTP, dCTP, and ddGTP;
   (ii) a A-termination mix comprising dGTP, dATP, TTP, dCTP, and ddATP;
   (iii) a T-termination mix comprising dGTP, dATP, TTP, dCTP, and ddTTP; and
   (iv) a C-termination mix comprising dGTP, dATP, TTP, dCTP, and ddCTP.

* * * * *

UNITED STATES PATENT AND TRADEMARK OFFICE
CERTIFICATE OF CORRECTION

PATENT NO. : 5,075,216
DATED : December 24, 1991
INVENTOR(S) : Innis, et al

It is certified that error appears in the above-indentified patent and that said Letters Patent is hereby corrected as shown below:

In column 5, in line 42, delete "dideoxynucleoside" and insert therefor --deoxynucleoside--.

In column 14, in line 63, delete "ESTA" and insert therefor --EDTA--.

In column 15, in line 8, delete "templatedependent" and insert therefor --template-dependent--;
in line 9, delete "dideoxynu-" and insert therefor --deoxynu--;
in line 19, delete "dideox" and insert therefor --deox--;
in line 22, delete "dideox" and insert therefor --deox--;
in line 25, delete "dideox" and insert therefor --deox--;
in line 29, delete "an asymmertric" and insert therefor --a--.

Signed and Sealed this

First Day of November, 1994

Attest:

BRUCE LEHMAN

Attesting Officer    Commissioner of Patents and Trademarks